(12) United States Patent
Ramanathan et al.

(10) Patent No.: US 6,468,757 B2
(45) Date of Patent: Oct. 22, 2002

(54) METHOD FOR DETERMINING DRUG-SERUM PROTEIN BINDING

(75) Inventors: Murali Ramanathan, Amherst, NY (US); Marilyn E. Morris, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/767,790

(22) Filed: Jan. 23, 2001

(65) Prior Publication Data

US 2001/0039005 A1 Nov. 8, 2001

Related U.S. Application Data

(60) Provisional application No. 60/177,936, filed on Jan. 25, 2000.

(51) Int. Cl.$^7$ .......................... C07H 21/04; G01N 33/53
(52) U.S. Cl. ........................................ 435/7.1; 536/23.1
(58) Field of Search .............................. 436/15, 16, 71, 436/87, 88, 165, 166, 805, 808, 815; 530/395, 402; 435/7.1; 536/23.1

(56) References Cited

PUBLICATIONS

Parikh et al., "A Rapid Spectrofluorimetric Technique for Determining Drug–Serum Protein Binding Suitable for High–Throughput Screening," *Pharmaceutical Research* 17(5):632–637 (2000).

Epps et al., "Determination of the Affinity of Drugs Toward Serum Albumin by Measurement of the Quenching of the Intrinsic Tryptophan Fluorescence of the Protein," *J. Pharm. Pharmacol.* 51:41–48 (1999).

Meagher et al., "Deconvolution of the Fluorescence Emission Spectrum of Human Antithrombin and Identification of the Tryptophan Residues that are Responsive to Heparin Binding," *J. Biol. Chem.* 273(6):23283–23289 (1998).

*Primary Examiner*—Andrew Wang
(74) *Attorney, Agent, or Firm*—Nixon Peabody LLP

(57) ABSTRACT

The present invention relates to a method of screening for drug binding to serum proteins by: preparing at least two solutions each including a concentration of a serum protein and a concentration of a candidate drug, wherein the concentration of the candidate drug is different for each of the at least two solutions; exposing each of the at least two solutions to a light source; measuring fluorescent emission by the serum protein or a serum protein-candidate drug complex for each of the at least two solutions upon said exposing; and determining whether a change in fluorescence emission is measured for an increased concentration of the candidate drug, wherein the change in fluorescence emission indicates binding of the candidate drug to the serum protein. A kit useful for performing a fluorimetric screening of drug binding to serum proteins is also disclosed.

32 Claims, 5 Drawing Sheets

METHOD FOR DETERMINING DRUG-SERUM PROTEIN BINDING

This application claims the benefit of U.S. Provisional Patent Application Serial No. 60/177,936, filed Jan. 25, 2000, which is hereby incorporated by reference in its entirety.

The work underlying this application was supported, at least in part, by NIGMS/NIH grant R29 GM54087. The U.S. Government may have certain rights in the invention.

FIELD OF THE INVENTION

The present invention relates to methods of screening for drug binding to serum proteins using spectrofluorimetry. Kits useful for performing fluorimetric screening of drug binding to serum proteins are also disclosed.

BACKGROUND OF THE INVENTION

Potent, pharmacologically active new drug candidates can be effective in vivo only if they are able to achieve and maintain therapeutic concentrations at the site of action. Pharmaceutical properties such as solubility, partition coefficient, permeability, and protein binding contribute to in vivo disposition and, frequently, these properties are important determinants of clinical outcome. The recent successes of combinatorial chemistry in accelerating drug discovery have also increased the interest in rapid, resource-sparing approaches to determining pharmaceutical properties.

The binding of drugs to serum proteins is particularly important, because it affects both the activity of drugs and their disposition (Huang et al., "Effect of Altered Disopyramide Binding on its Pharmacologic Response in Rabbits," *Journal of Pharmacology & Experimental Therapeutics*, 223:469–71 (1982); Qin et al., "Decreased Elimination of Drug in the Presence of Alpha-1-acid Glycoprotein is Related to a Reduced Hepatocyte Uptake," *Journal of Pharmacology & Experimental Therapeutics*, 269:1176–81 (1994)). According to the "free drug" hypothesis, only unbound drug exerts pharmacological activity (Recant et al., "Thyroid Function in Nephrosis," *Journal of Clinical Investigation*, 31:789 (1952)) and disposition is often altered by drug binding (Shand et al., "Perfusion-Limited of Plasma Drug Binding on Hepatic Drug Extraction," *Life Sciences*, 19:125–30 (1976); Jansen, "Influence of Plasma Protein Binding Kinetics on Hepatic Clearance Assessed from a "Tube" Model and a "Well-stirred" Model," *Journal of Pharmacokinetics & Biopharmaceutics*, 9:15–26 (1981)). Consequently, it is important to know the affinity of a drug for serum proteins.

A variety of techniques have been proposed for protein binding measurements including dialysis, ultrafiltration (Huang, "Errors in Estimating the Unbound Fraction of Drugs Due to the Volume Shift in Equilibrium Dialysis," *Journal of Pharmaceutical Sciences*, 72:1368–9 (1983)), circular dichroism (Ascoli et al., "Stereospecific and Competitive Binding of Drugs to Human Serum Albumin: A Difference Circular Dichroism Approach," *Journal of Pharmaceutical Sciences*, 84:737–41 (1995)), and extrinsic fluorescence (Sudlow et al., "Spectroscopic Techniques in the Study of Protein Binding: The Use of 1-Anilino-8-Naphthalenesulphonate as a Fluorescent Probe for the Study of the Binding of Iophenoxic and Iopanoic Acids to Human Serum Albumin," *Molecular Pharmacology*, 9:649–57 (1973); Sudlow et al., "The Characterization of Two Specific Drug Binding Sites on Human Serum Albumin," *Molecular Pharmacology*, 11:824–32 (1975); Epps et al., "A General, Wide-range Spectrofluorometric Method for Measuring the Site-Specific Affinities of Drugs Toward Human Serum Albumin," *Analytical Biochemistry*, 227:342–50 (1995); Suarez Varela et al., "Spectrofluorimetric Study of the Binding of 1-Anilnonaphthalene-8-Sulfonate to Bovine Serum Albumin," *Journal of Pharmaceutical Sciences*, 81:843–4 (1992)). Despite the fact that the displacement of extrinsic fluorophores such as warfarin and dansylglycine has been proposed as the basis for a rapid protein binding assay (Epps et al., "A General, Wide-range Spectrofluorometric Method for Measuring the Site-Specific Affinities of Drugs Toward Human Serum Albumin," *Analytical Biochemistry*, 227:342–50 (1995)) and the fact that such assays are drug nonspecific and rapid, they are indirect because they utilize the interaction between two drugs to produce an extrinsic signal.

The present invention is directed to overcoming these deficiencies in the art.

SUMMARY OF THE INVENTION

The present invention relates to a method of screening for drug binding to serum proteins. This method includes preparing at least two solutions, each of the at least two solutions containing a concentration of a serum protein characterized by broad specificity in binding to xenobiotics and a concentration of a candidate drug, wherein the concentration of the candidate drug is different for each of the at least two solutions and, optionally, one of the at least two solutions is a control solution characterized by a candidate drug concentration of zero; exposing each of the at least two solutions to a light source; measuring fluorescent emission by the serum protein or a serum protein-candidate drug complex for each of the at least two solutions upon the exposing; and determining whether a change in fluorescence emission is measured for an increased concentration of the candidate drug, wherein the change in fluorescence emission indicates binding of the candidate drug to the serum protein.

The present invention also relates to a method of screening for drug binding to serum proteins, where a dissociation constant ($Kd$) for the candidate drug and the serum protein can be calculated based on the measured fluorescence emissions. This method includes preparing at least two solutions, each of the at least two solutions containing a concentration of a serum protein characterized by broad specificity in binding to xenobiotics and a concentration of a candidate drug, wherein the concentration of the candidate drug is different for each of the at least two solutions and, optionally, one of the at least two solutions is a control solution characterized by a candidate drug concentration of zero; exposing each of the at least two solutions to a light source; measuring fluorescent emission by the serum protein or a serum protein-candidate drug complex for each of the at least two solutions upon the exposing; and calculating a dissociation constant ($Kd$) for the candidate drug and the serum protein based on the measured fluorescence emissions.

Another aspect of the present invention relates to a kit useful for performing a fluorimetric screening of drug binding to serum proteins. The kit includes a plurality of detection cells compatible for use with a fluorimetric device, one or more solutions each having a predetermined concentration of a serum protein characterized by broad specificity in binding to xenobiotics, and instructions for combining a volume of the one or more solutions with a quantity of a drug in the detection cells, exposing the detection cells to the fluorimetric device, and analyzing fluorimetric emission data.

The present invention uses spectrofluorimetry, a technique that has been widely used to study biomolecular interactions and which has many advantages over other techniques such as dialysis and ultrafiltration. The advantages arise primarily because fluorescence data are obtained without separating the bound and unbound species, which reduces the time required for the experiment and eliminates the need for a size-selective membrane. The dialysis and ultrafiltration methods require analysis of free and total drug concentration which can be resource and time consuming. Additionally, these methods cannot be used with drugs that bind extensively to the membrane (MacKichan, "Influence of Protein Binding and Use of Unbound (Free) Drug Concentrations" in *Applied Pharmacokinetics: Principles of Therapeutic Drug Monitoring*, pp 5.1–5.48, Evans et al. (eds.), Applied Therapeutics, Vancouver, Wash., (1992), which is hereby incorporated by reference in its entirety); this is often a serious problem with highly hydrophobic drugs. Although the displacement of extrinsic fluorophores such as warfarin and dansylglycine has been proposed as the basis for a rapid protein binding assay (Epps et al., "A General, Wide-range Spectrofluorometric Method for Measuring the Site-Specific Affinities of Drugs Toward Human Serum Albumin," *Analytical Biochemistry*, 227:342–50 (1995), which is hereby incorporated by reference in its entirety), intrinsic fluorescence offers advantages over extrinsic fluorescence and has the potential to yield better estimates of a dissociation constant (K$d$) when, for example, the drug of interest is physically incompatible with the fluorophores or if there are interactions between the binding sites. Physical incompatibility could occur, for example, if the drug of interest caused the fluorophore to precipitate. The present invention also requires only small sample volumes, is amenable to automation, and may be carried out using a multiwell format. Finally, the present invention is not compound specific and, thus, does not require specific drug analysis such as analytical chromatography or mass spectrometry for quantitation.

DETAILED DESCRIPTION OF THE INVENTION

Figure 1A:
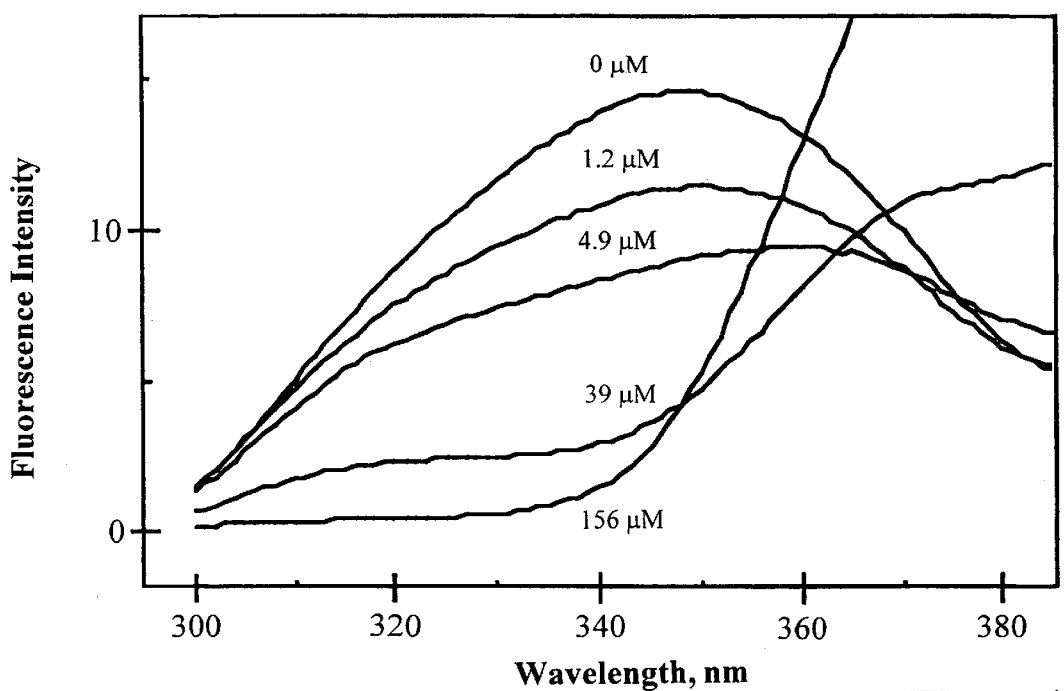
FIG. 1A shows the emission spectra of human serum albumin (HSA) in the absence and presence of the indicated concentrations of RS sodium warfarin.

The present invention relates to a method of screening for drug binding to serum proteins. This method includes the steps of first preparing at least two solutions, each of which contains a concentration of a serum protein characterized by broad specificity in binding to xenobiotics and a concentration of a candidate drug. The concentration of the candidate drug is different for each of the at least two solutions and, optionally, one of the at least two solutions is a control solution characterized by a candidate drug concentration of zero. Each of the at least two solutions are then exposed to a light source and fluorescent emission by the serum protein or a serum protein-candidate drug complex is measured for each of the at least two solutions. It is then determined whether a change in fluorescence emission was measured for an increased concentration of the candidate drug, where the change in fluorescence emission indicates binding of the candidate drug to the serum protein.

Each of the at least two solutions can be prepared, e.g., by serially diluting stock solutions of candidate drugs in a solution with a fixed concentration of the serum protein. Other methods of diluting the candidate drug solution can also be employed. The stock solutions can be prepared either as an aqueous solution or a non-aqueous solution.

Suitable aqueous solutions can be prepared using, for example, water or phosphate-buffered saline (PBS) as solvents.

Suitable non-aqueous solutions can be prepared using dimethyl sulfoxide (DMSO) or ethanol (less than about 5% by vol.) as solvents.

As used herein, "serum protein" refers specifically to drug-binding serum proteins which are characterized by broad specificity in binding to xenobiotics in solution. Thus, to be useful for screening candidate drugs, the serum proteins employed in the present invention should have one or more binding sites, where the binding sites either individually or collectively have broad specificity, enabling the serum protein to bind to a large and diverse population of drugs. The serum proteins preferably include one or more tryptophan or tyrosine residues capable of fluorescence when exposed to excitatory light. A single serum protein can be used alone or a combination of serum proteins can be used together in solution.

The serum protein can be a mammalian serum protein, but preferably a human serum protein. Many serum proteins are commercially available. Serum proteins can otherwise be substantially purified, using known techniques, from suitable sera such as whole blood, lymph, plasma, etc. Alternatively, serum proteins can be recombinantly expressed from suitable host cells, e.g., *E. coli*, and then isolated and purified from a growth medium using known procedures.

The serum proteins, as defined above, fall into several different classes including, without limitation, albumins, glycoproteins, and lipoproteins. An exemplary glycoprotein is, without limitation thereto, $\alpha_1$-acid glycoprotein (AAG). Exemplary lipoproteins include, but are not limited to, very low density lipoproteins (VLDL), low density lipoproteins (LDL), and high density lipoproteins (HDL).

According to a preferred embodiment of the present invention, the serum protein is human serum albumin (HSA), human AAG, or a combination thereof. Both of these serum proteins are important plasma transport proteins.

The concentration of the serum protein in each of the at least two solutions can be substantially the same. Fluorescence methods of the present invention are preferably accompanied by the use of low, non-physiological concentrations of the serum protein. The lower serum protein concentrations are employed to avoid the non-linearities caused by the inner filter effect. The inner filter effect occurs when a significant portion of the excitation light is absorbed by high concentration of the sample solution, whereby successively deeper volumes of the sample are excited by a different spectral distribution of light that has been depleted (by preceding volumes of the sample). Consequently, there are problems with using the higher, physiological concentrations of serum proteins (e.g., about 35–55 g/L for HSA and about 0.55–1.40 g/L for AAG). The inner filter effect also occurs when the dimensions of the detection cells containing the solutions provide a long light path and the solution closest to the light source filters out the excitation light such that the solution farthest from the light source is excited at a reduced level.

To minimize the impact of the inner filter effect, a number of strategies can be employed. First, as noted above, low, non-physiological concentrations of serum protein can be employed. Second, a modified solution container can be employed, such as a cuvet which modifies the depth of the solution through which light must travel. Third, the inner filter effect can usually be compensated for by making concurrent absorbance measurements (Lakowicz, *Principles of Fluorescence Spectroscopy*, Plenum Press, New York, N.Y., (1983), which is hereby incorporated by reference in its entirety), although additional absorbance measurements would add another step to the screen and potentially reduce its throughput.

After the control and test solutions are prepared, the fluorescence emission from each of the at least two solutions can be measured with a fluorimeter.

The excitation wavelength and the wavelength of emission maxima for specific serum proteins will depend upon the particular amino acids residues they contain (either tryptophan or tyrosine). Maximal fluorescence of tyrosine residues can be achieved with excitation light having a wavelength of about 265 nm, whereas maximal fluorescence of tryptophan residues can be achieved with excitation light having a wavelength of about 295 nm. To achieve suitable fluorescence emission from both tyrosine and tryptophan residues (assuming both are present in a particular serum protein in solution), excitation light having a wavelength of about 280 nm can be employed. Tyrosine residues are characterized by maximal fluorescence emission at about 305 nm and tryptophan residues are characterized by maximal fluorescence emission at about 340 nm. To identify emissions from these residues, either emissions within a narrow bandwidth of these emission maxima (e.g.,±5 nm) or emissions within a broad bandwidth (e.g., from about 300 to about 400 nm) can be examined.

A preferred measurement of intrinsic fluorescence can be achieved by measuring the fluorescence emissions of serum proteins alone. Another preferred measurement of intrinsic fluorescence can be achieved by measuring the fluorescence emissions of the candidate drug serum protein complex alone. Both of these intrinsic fluorescence emissions can also be measured simultaneously. By examining the spectral emissions at different excitation or emission wavelengths, the fluorescent emissions caused by the serum protein and the candidate drug-serum protein complex can be elucidated directly. When the spectral properties of the solution render it difficult to discern the emissions caused by the candidate drug-serum protein complex versus the serum protein (i.e., some overlap in their spectral emissions), spectroscopic component analysis can be used to identify the effects of each individual contributor of fluorescent emission in the detected spectrum. One of skill in the art can perform spectroscopic component analysis according to any one of a number of such techniques.

In certain circumstances, it may also be desirable to identify the emission corresponding to the candidate drug, assuming it too fluoresces. Typically, direct measurements of all three emissions are possible when the fluorescence emissions of the serum protein, candidate drug, and candidate drug-serum protein complex are sufficiently distinct of one another such that the component effects on the spectral emissions can be assessed. Where some overlap exists, spectroscopic component analysis can be used to identify the effects of each individual contributor of fluorescent emission in the detected spectrum.

Thus, according to the present invention, intrinsic fluorescence of the serum protein can be measured as either the fluorescence caused by unbound serum protein, bound serum protein (i.e., candidate drug-serum protein complex), or a combination thereof. Moreover, extrinsic measurements of candidate drug fluorescence can also be performed in addition to any of the intrinsic measurements.

A change in the measured fluorescence emission, i.e., from one solution to another solution having a different concentration of the candidate drug, indicates binding of the candidate drug to the serum protein.

For example, when measuring the intrinsic fluorescence emissions of the serum protein alone, maximum emissions at a particular wavelength will be detected in a control solution containing no candidate drug. Reductions in the fluorescent emissions of the serum protein will be detected as any available candidate drug binds to the serum protein to form a complex. The actual emission measurements (i.e., from the at least two solutions) can be plotted against the total drug concentration to illustrate the quenching of fluorescence by drug binding. Based on the actual measurements, the percent quenching can be determined for particular drug concentrations or maximal quenching can be determined by assessing when substantially no further quenching occurs for subsequent increases in candidate drug concentration. The determination of maximal quenching can be used to calculate the minimum effective dose required for a particular candidate drug given the relative concentrations of serum protein in the at least two solutions and serum protein at physiological levels.

Alternatively, when measuring the intrinsic fluorescence emissions of the candidate drug-serum protein complex alone, minimum emissions at a particular wavelength (typically only background) will be detected in a control solution containing no candidate drug. Increases in fluorescent emissions will be detected as any available candidate drug binds to the serum protein to form a complex. The actual emission measurements (i.e., from the at least two solutions) can be plotted against the total drug concentration to illustrate the enhanced fluorescence upon drug binding. As above, maximal fluorescence (as opposed to maximal quenching) can be determined.

In addition to the above measurements, it is also useful to determine the dissociation constant ($Kd$) for the candidate drug and the serum protein. The $Kd$ value can be calculated based on the measured fluorescence emissions. According to the quadratic binding equation:

$$D_b = \frac{S - \sqrt{S^2 - 4D_T P_T}}{2} \quad \text{(Eq. 1)}$$

$D_b$ is the concentration of the candidate drug-serum protein complex, $D_T$ is the total drug concentration, $P_T$ is the total protein concentration, and S equals $D_T + P_T + K_d$, where $K_d$ is the dissociation constant.

Without loss of generality, the observed fluorescence F, is related to the molar concentrations of the candidate drug-serum protein complex $D_b$, free drug $D_f$ and free protein $P_f$, and their respective specific fluorescence values, $f_1$, $f_2$, and $f_3$.

$$F = f_1 D_b + f_2 D_f + f_3 P_f \quad \text{(Eq. 2)}$$

$$F = f_1 D_b + f_2 (D_T - D_b) + f_3 (P_T - D_b) \quad \text{(Eq. 3)}$$

$$F = (f_1 - f_2 - f_3) D_b + f_2 D_T + f_3 P_T \quad \text{(Eq. 4)}$$

But $f_3 P_T$ equals $F_0$, the fluorescence of serum protein alone in the absence of the candidate drug (control). Thus, after rearranging:

$$\frac{F_o - F}{F_o} = \% \text{ Quenching} = \frac{(f_2 + f_3 - f_1)}{f_3} \frac{D_b}{P_T} - \frac{f_2}{f_3} \frac{D_T}{P_T} \quad \text{(Eq. 5)}$$

The $(f_2 + f_3 - f_1)/f_3$ and $f_2/f_3$ terms are constants and since $P_T$ is a constant under the chosen experimental conditions, the constants can be absorbed into new constants $C_1$ and $C_2$.

$$\% \text{ Quenching} = C_1 \left( \frac{S - \sqrt{S^2 - 4D_T P_T}}{2} \right) - C_2 D_T \quad \text{(Eq. 6)}$$

Thus, the quadratic binding equation for fluorescence quenching (Eq. 6) has three fitted parameters, $C_1$, $C_2$, and $K_d$. The unknown parameters, particularly $K_d$, can be calculated from conducting a least squares curve fitting of plots of % Quenching vs. $D_T$.

As a result of calculating the dissociation constant ($K_d$) for a particular drug and serum protein, the binding characteristics of the drug and serum protein can be fairly characterized. Generally, a $K_d$ of less than about 50 µM indicates that the candidate drug is very strongly bound to the serum protein; a $K_d$ of more than about 50 µM and less than about 100 µM indicates that the candidate drug is strongly bound to the serum protein; a $K_d$ of more than about 100 µM and less than about 250 µM indicates that the candidate drug is intermediately bound to the serum protein; and a $K_d$ of more than about 250 µM indicates that the candidate drug is not significantly bound to the serum protein.

Fluorescence methods differ from ultrafiltration and equilibrium dialysis in that the extent of serum binding is inferred from the $K_d$ estimates. An empirical alternative to the calculation of $K_d$ as described above involves the use of known standards. For example, measuring the fluorescent emission in the presence of candidate drugs can be carried out simultaneously with measuring the fluorescent emission in the presence of several drugs with known extents of plasma binding (as positive controls within the experiment). The quenching curve for the candidate drug of interest can be compared directly to those of the controls.

The present invention can also be useful for screening combinatorial libraries where the candidate drug is one of a plurality of candidate drugs. This method includes the steps of preparing a series of the at least two solutions for each of the plurality of candidate drugs, exposing each of the at least two solutions to a light source, measuring fluorescent emission by the serum protein or the serum proteincandidate drug complex for each of the at least two solutions, and determining for each of the plurality of candidate drugs whether a change in fluorescence emission is measured for an increased concentration of the candidate drug. The steps of exposing and measuring in this case are conveniently carried out in a multiwell format.

Figure 6:
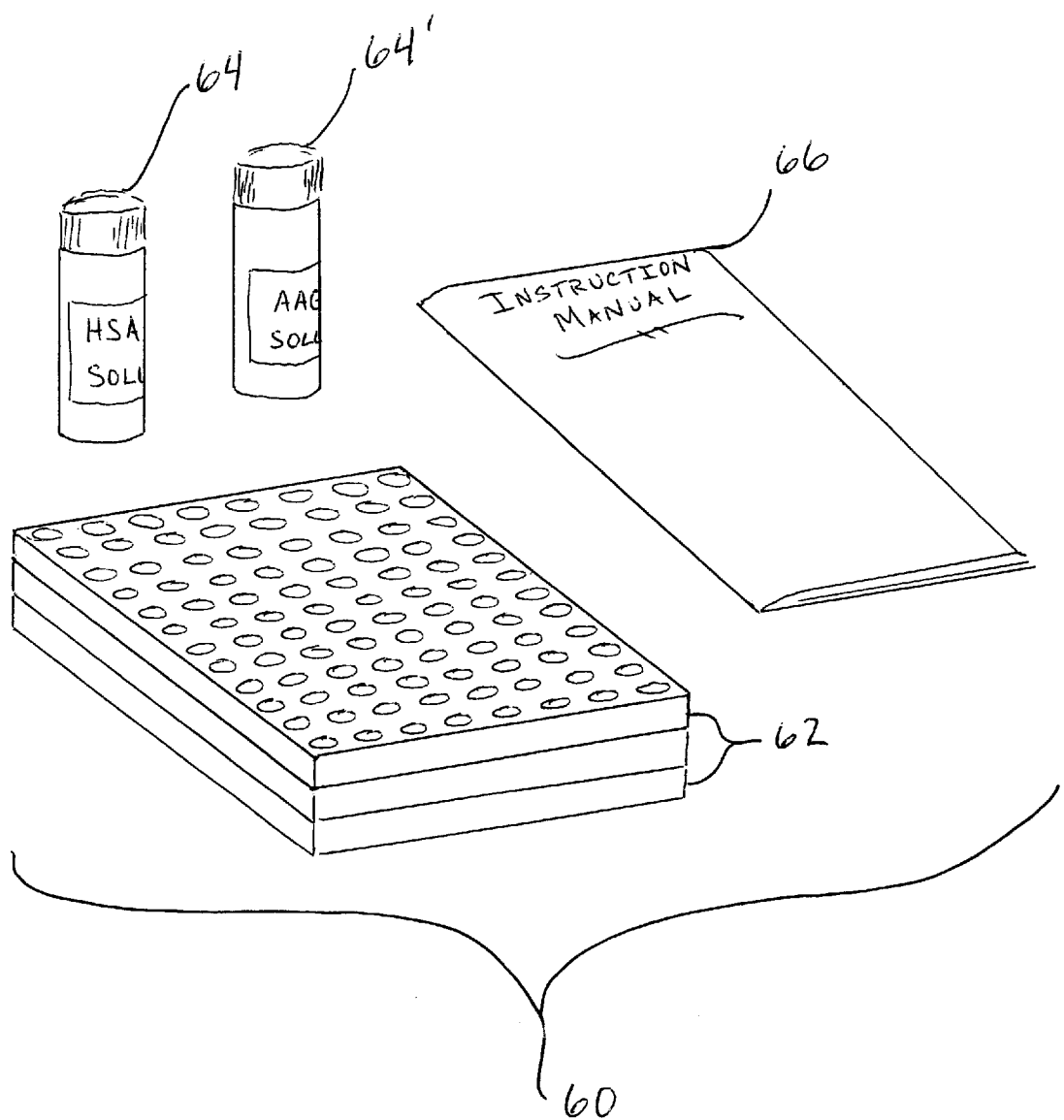
FIG. 6 illustrates the components of a kit which can be used to perform intrinsic fluorescence analysis of candidate drug-serum protein binding in accordance with the present invention.

Another aspect of the present invention relates to a kit useful for performing a fluorimetric screening of drug binding to serum proteins. As shown in FIG. 6, for example, the kit 60 includes a plurality of detection cells such as cuvettes or multiwell plates 62 compatible for use with a fluorimetric device, one or more solutions 64, 64' each having a predetermined concentration of a serum protein, and instructions 66 for combining a volume of the one or more solutions with a quantity of a drug in the detection cells, exposing the detection cells to the fluorimetric device, and analyzing fluorimetric emission data in accordance with the present invention.

EXAMPLES

The following examples are provided to illustrate embodiments of the present invention but are by no means intended to limit its scope.

Materials

In the following examples, use of the following materials is disclosed. Human serum albumin (HSA), $\alpha_1$-acid glycoprotein (AAG), acetaminophen, chloramphenicol, chlorpromazine hydrochloride, iophenoxic acid, imipramine hydrochloride, phenylbutazone and (±) sulfinpyrazone were obtained from Sigma Chemicals (St. Louis, Mo.); sodium salicylate, lithium chloride and dimethyl sulfoxide (DMSO) were obtained from Fisher Scientific (Pittsburgh, Pa.); ampicillin was obtained from Apothecon; diazepam was obtained from Hoffman-La Roche (Nutley, N.J.); and theophylline was obtained from Nutritional Biochemicals Corporation (Cleveland, Ohio). The R, S, and RS enantiomers of sodium warfarin were from Endo Laboratories (Garden City, N.Y.). Dulbecco's phosphate buffered saline (D-PBS) was purchased from Life Technologies (Grand Island, N.Y.).

Example 1—Fluorescence Spectroscopy

All fluorescence studies were performed at room temperature on a SLM Aminco 8000 fluorometer (Spectronic Unicam, Rochester, N.Y.) with 4 mm excitation and emission slits.

Tryptophan fluorescence emission spectra over the 300–400 nm wavelength range were recorded with the excitation wavelength set at 280 nm. A 295 nm long pass filter was used during the measurements to minimize the effect of Raman bands on the emission maxima. Spectra were recorded using the 2 mm path in I-shaped, 2 mm/10 mm dual path length cuvettes to minimize the contributions of the inner filter effect.

HSA and AAG were dissolved in D-PBS at a concentration of 2.02 µM. Stock solutions of sodium warfarin (R, RS, S), lithium chloride, ampicillin, phenylbutazone, iophenoxic acid, imipramine hydrochloride and sodium salicylate were prepared in D-PBS while the diazepam, sulfinpyrazone, theophylline, chloramphenicol, acetaminophen and chlorpromazine hydrochloride were prepared in DMSO. For titrations, solutions were prepared by serially diluting the stock solution in 2.02 μM HSA (or AAG). The solutions were mixed and, after allowing 30 minutes at room temperature for equilibration, the spectra were recorded. The percent reduction in fluorescence (% Quenching) was plotted against total drug concentration, $D_T$. The quadratic binding equation (Eq. 6) was used for fitting instead of the Michaelis-Menten type simple binding hyperbola, because under the experimental conditions used, the free drug concentration is not measured (Epps et al., "A General, Wide-range Spectrofluorometric Method for Measuring the Site-Specific Affinities of Drugs Toward Human Serum Albumin," *Analytical Biochemistry*, 227:342–50 (1995); Balasubramanian et al., "Interferon-gamma-inhibitory Oligodeoxynucleotides Alter the Conformation of Interferon-gamma," *Molecular Pharmacology*, 53:926–32 (1998), which are hereby incorporated by reference in their entirety).

The quadratic binding equation for fluorescence quenching (Eq. 6) has 3 fitted parameters, $C_1$, $C_2$, and $K_d$. The least squares curve fitting routine in Kaleidagraph 3.08 (Synergy Software, Reading Pa.) was used to determine the unknown parameters, including $K_d$, from plots of % Quenching vs. $D_T$. The program manual accompanying Kaleidagraph 3.08 is hereby incorporated by reference in its entirety.

Sample preparation for the experiments employing multiwell plates was analogous. The samples (200 μl) were transferred to black 96-well plates and read on a Spectral-Max Gemini fluorescence microplate reader (Molecular Dynamics, Sunnyvale, Calif.) with excitation and emission wavelengths of 280 nm and 340 nm, respectively. Data were analyzed using the % Quenching equation with the linear term set to zero because the additional linear term $C_2$, was not significant, i.e., its confidence intervals spanned the origin. The changes in the $K_d$ estimates, with and without the linear term, were not statistically significant.

In the following examples, all the $K_d$ values are reported in the form, average $K_d±$ average standard error of the $K_d$ estimate, and these terms respectively refer to the arithmetic means of the $K_d$ and standard error estimates obtained from separately fitting data from multiple experiments.

Example 2—Intrinsic Fluorescence Quenching of HSA Measures Binding to the Warfarin Site The warfarin binding site is a distinct drug binding site that has been identified on HSA and is used by drugs such as phenylbutazone, sulfonamides, phenytoin, and valproic acid. Because fluorescence quenching measures the response of only the amino acids tryptophan and—to a lesser extent—tyrosine, the feasibility and sensitivity of the present method was challenged by testing the hypothesis that warfarin binding to the warfarin binding site would result in concentration-dependent fluorescence quenching of HSA emissions. Sodium warfarin was selected as a probe for the site and FIG. 1A shows fluorescence spectra of 2.02 μM HSA in PBS in the presence of varying concentrations of sodium warfarin. The spectra show concentration-dependent decreases in HSA fluorescence. The fluorescence peak of HSA alone was at 342 nm which suggests that the average-environment of the two tryptophans is shielded from the surrounding water molecules. At higher drug concentrations, an additional peak corresponding to the fluorescence of the drug appeared at longer wavelengths.

Figure 1B:
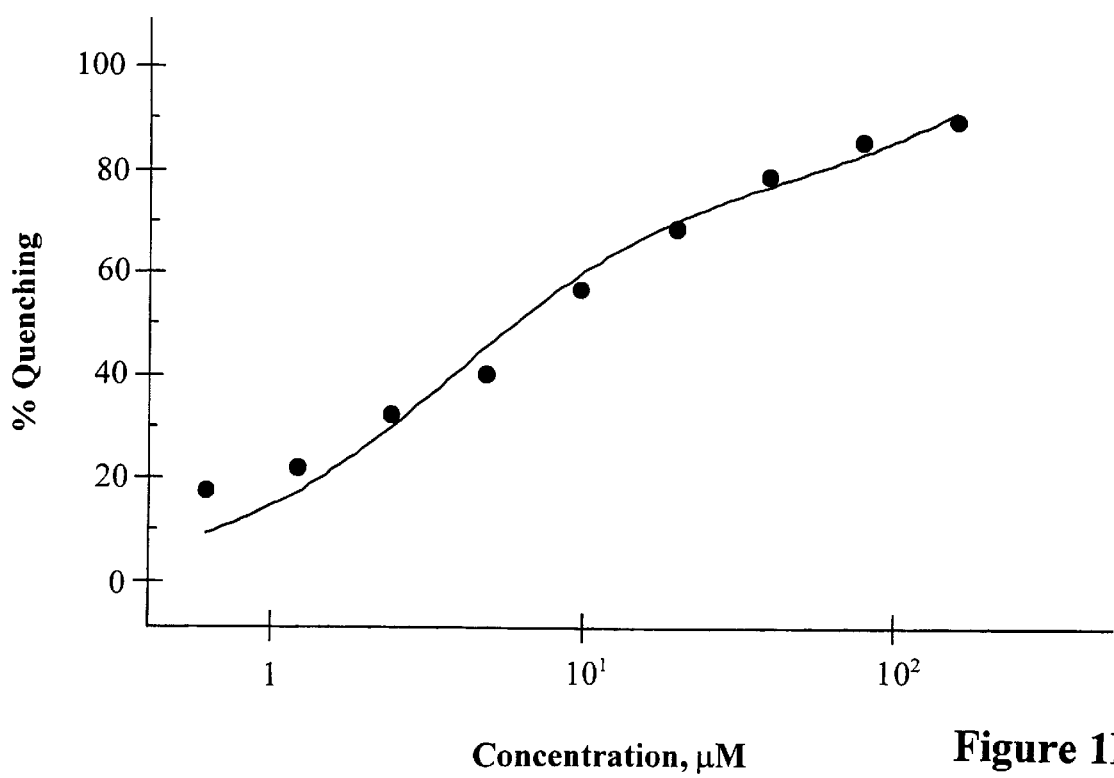
FIG. 1B plots the percent quenching as a function of the RS sodium warfarin concentration. The solid line is the best fit quadratic binding curve.

FIG. 1B shows the percent quenching at 340 nm as a function of drug concentration. The data in FIG. 1B shows linearity at low drug concentrations and saturation at high drug concentrations—characteristics usually associated with specific binding to proteins. The data were fitted to a quadratic binding equation and the average $K_d$ (± average error) value was found to be 5.3±1.5 μM using the cuvet method and 6.8±1.5 μM using the multiwell format. These results showed that the warfarin binding site responded to drug binding with changes in fluorescence quenching.

Example 3—Intrinsic Fluorescence Quenching of HSA Measures Binding to the Benzodiazepine Site The benzodiazepine binding site on HSA binds drugs such as diazepam, probenicid, and the penicillins and is the other distinct drug binding site on HSA. The hypothesis that HSA fluorescence is modulated by drug binding to the benzodiazepine site was tested using diazepam as a probe for this site.

Figure 2A:
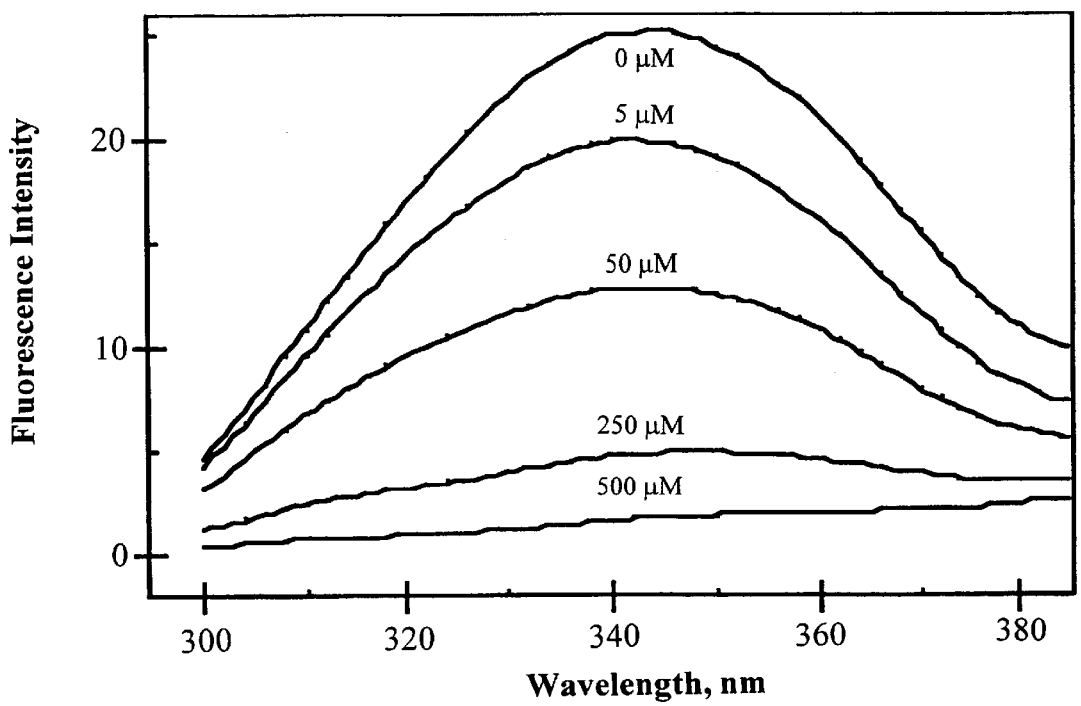
FIG. 2A shows the emission spectra of HSA in the absence and presence of the indicated concentrations of diazepam.
Figure 2B:
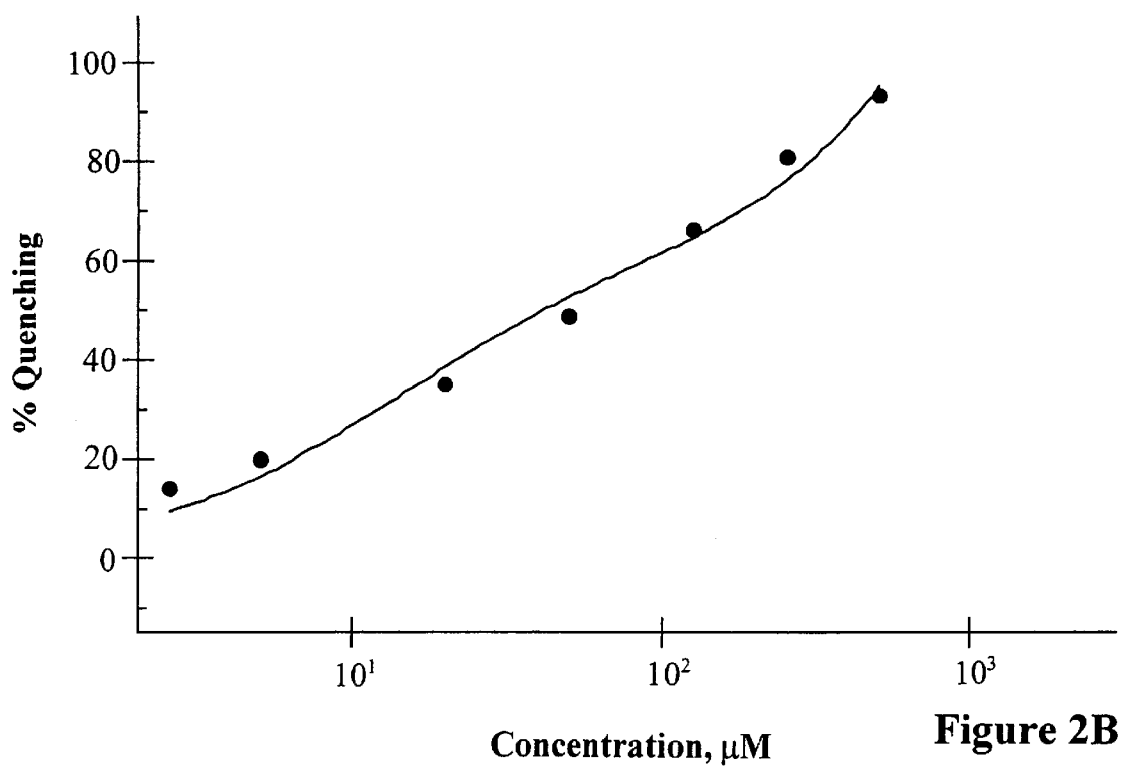
FIG. 2B is the corresponding percent quenching curve. The solid line is the best fit quadratic binding curve.

FIG. 2A shows the fluorescence spectra for 2.02 μM HSA in the absence and presence of varying diazepam concentrations. The spectra showed concentration-dependent changes in fluorescence intensity. The peak position did not shift, suggesting that the hydrophobicity changes that occurred on drug binding were either negligible or were offset. The percent quenching curve at 340 nm is shown in FIG. 2B. The quenching curve shows saturation as a function of drug concentration and $K_d$ obtained by fitting a quadratic binding curve was 12±4.7 μM. The $K_d$ value using the multiwell format was 28±4 μM. The exact reasons for the relatively small, 2.3-fold discrepancy between the multiwell and cuvet methods for this drug were unclear.

Example 4—Intrinsic Fluorescence Quenching of HSA Measures Binding of Acidic Drugs Because HSA commonly binds acidic drugs, the generality of the present method was challenged by testing the hypothesis that the binding of sodium salicylate, a salt of salicylic acid, would quench HSA fluorescence in a concentration-dependent manner.

Figure 3:
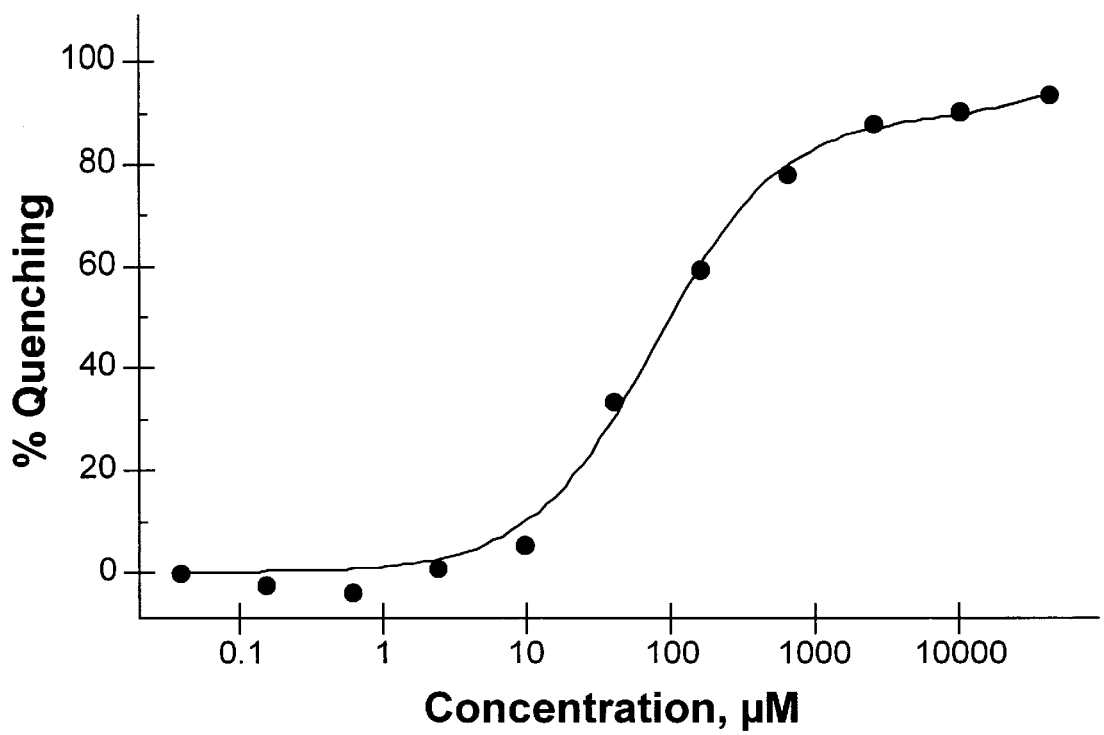
FIG. 3 shows the percent quenching curve for salicylic acid. The solid line is the best fit quadratic binding curve.

The percent quenching of HSA in the presence of sodium salicylate is shown in FIG. 3. The quenching curve showed saturation and demonstrated that the intrinsic fluorescence of HSA was modulated by the binding of salicylate. From the fitting, a $K_d$ of 76±8.5 ΞM was estimated for the cuvet method. The experiments in the multiwell format yielded a $K_d$ of 71±12 μM.

Example 5—Intrinsic Fluorescence Quenching of HSA is not Altered by DMSO

Figure 4:
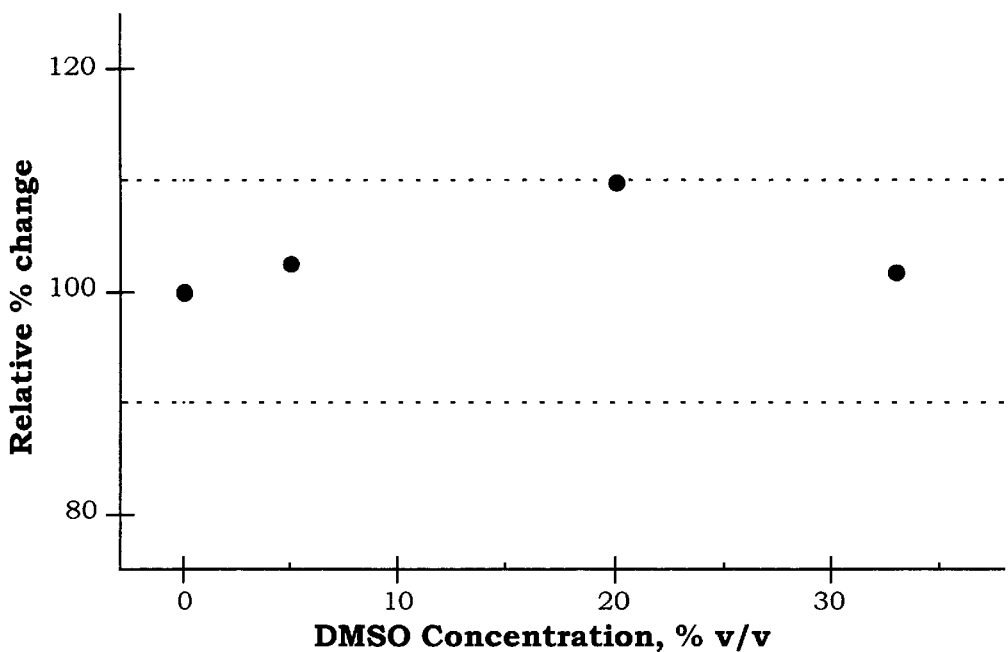
FIG. 4 shows the emission spectra of HSA in the presence of varying concentrations (0–30% v/v) of the organic solvent dimethyl sulfoxide (DMSO). The emission spectra are relative to HSA fluorescence in the absence of DMSO. The dashed lines represent 90% and 110% relative fluorescence and are included for reference.

Frequently, drugs in development have poor aqueous solubility and stock solutions are prepared in DMSO. To extend the usefulness of the present method for drug development applications, the effects of DMSO on HSA fluorescence quenching were tested. As illustrated in FIG. 4, over a concentration range of 0–30% v/v, DMSO did not quench HSA intrinsic fluorescence. Therefore, the method of the present invention is applicable to both aqueous solutions and organic solutions such as DMSO.

Example 6—Intrinsic Fluorescence Quenching of AAG is Altered on Drug Binding

Figure 5A:
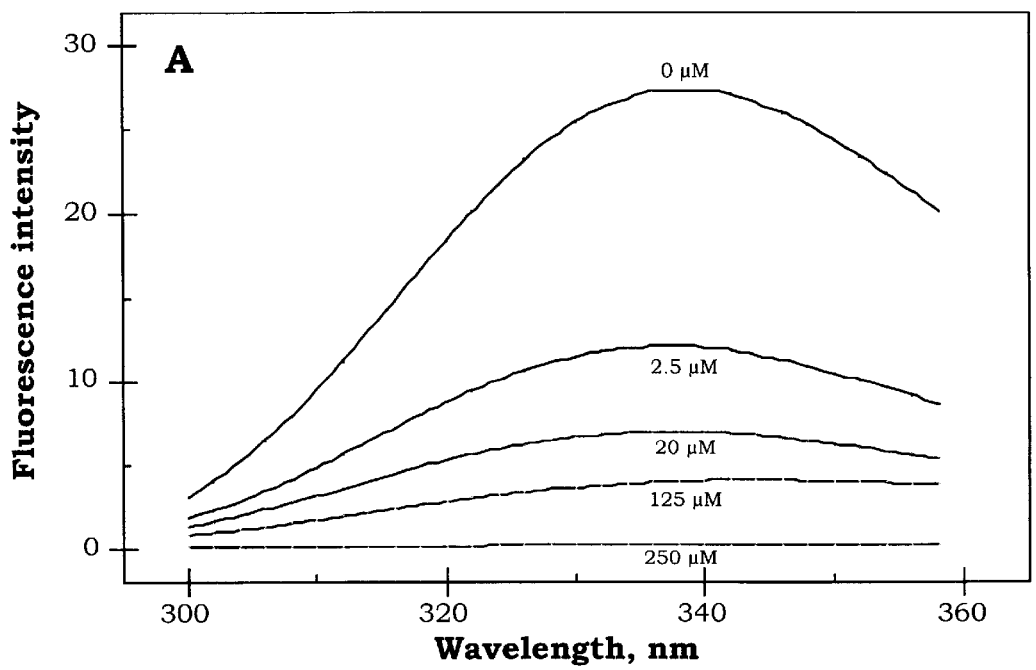
FIG. 5A shows the emission spectra of $\alpha_1$-acid glycoprotein (AAG) in the absence and presence of the indicated concentrations of chlorpromazine hydrochloride.
Figure 5B:
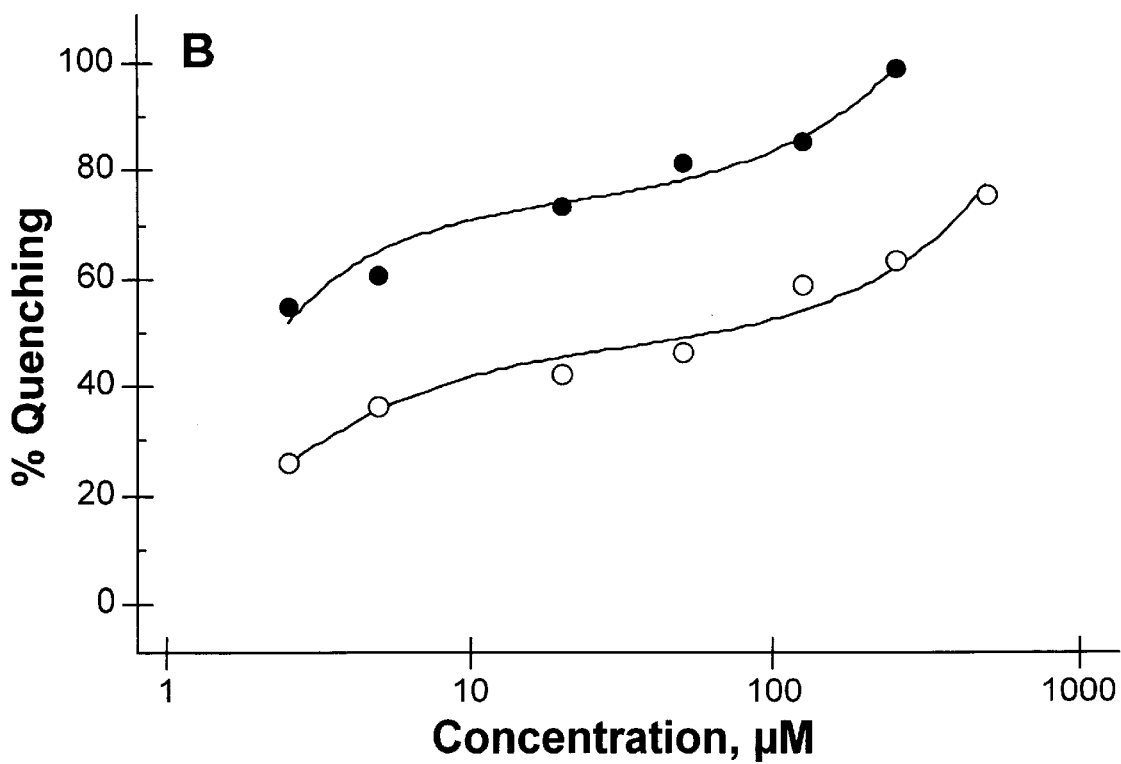
FIG. 5B is the corresponding percent quenching curve for imapramine hydrochloride (open circles) and chlorpromazine hydrochloride (filled circles). The solid line is the best fit quadratic binding curve.

AAG is present in serum at much lower concentrations than HAS and often binds certain drugs with high affinity (MacKichan, "Influence of Protein Binding and Use of Unbound (Free) Drug Concentrations" in *Applied Pharmacokinetics: Principles of Therapeutic Drug Monitoring*, pp 5.1–5.48, Evans et al. (eds.), Applied Therapeutics, Vancouver, Wash., (1992), which is hereby incorporated by reference in its entirety). Binding of drugs to AAG may also affect the environment of tryptophan residues and cause concentration-dependent fluorescence quenching of AAG spectra. Chlorpromazine hydrochloride was selected to test this hypothesis and FIG. 5A shows fluorescence spectra of 2.02 $\mu$M AAG in PBS in the presence of varying concentrations of chlorpromazine hydrochloride. The spectra show concentration-dependent decreases in AAG fluorescence. FIG. 5B shows the percent quenching at 340 nm as a function of drug concentration. The data were fitted to a quadratic binding equation and the $K_d$ value was found to be 0.47±0.18 $\mu$M. These results showed that the AAG drug binding site responded to chlorpromazine hydrochloride.

To confirm that the quenching of AAG fluorescence was not unique to chlorpromazine hydrochloride, experiments were carried out with another drug, imipramine hydrochloride. As shown in FIG. 5B, concentration-dependent quenching was observed again with a $K_d$ value of 1.2±0.44 $\mu$M.

Example 7—Comparison of Intrinsic Fluorescence Measurements to Extrinsic Fluorescence Methodology Epps et al. proposed extrinsic fluorescence based assay for measuring drug binding to HSA (Epps et al., "A General, Wide-range Spectrofluorometric Method for Measuring the Site-Specific Affinities of Drugs Toward Human Serum Albumin," *Analytical Biochemistry*, 227:342–50 (1995), which is hereby incorporated by reference in its entirety). To validate the intrinsic fluorescence based method proposed to the extrinsic fluorescence based technique, experiments were carried out with three drugs, phenylbutazone, diazepam, and warfarin sodium, whose dissociation constants were reported by Epps et al. The results in Table 1 below compare the dissociation constants obtained using the two techniques. With the cuvet method, the dissociation constants for warfarin sodium and diazepam were fairly close to those estimated by Epps et al. but the intrinsic fluorescence estimate for the dissociation constant for phenylbutazone was approximately six-fold greater than that estimated from the extrinsic fluorescence method. The exact reasons for the four to six-fold discrepancy in dissociation constants of phenylbutazone and diazepam are unknown.

TABLE 1

Comparison of the Extrinsic and Intrinsic Fluorescence Methods

| Drug | Intrinsic Fluorescence $K_d$ values ($\mu$M) | | Extrinsic Fluorescence[‡] $K_d$ values ($\mu$M) |
|---|---|---|---|
| | Cuvet | Multiwell | |
| RS sodium warfarin | 5.3 ± 1.5 | 6.8 ± 1.5 | 3.4 ± 0.69 |
| Diazepam | 12. ± 4.7 | 28 ± 4.0 | 7.7 ± 1.0 |
| Phenylbutazone | 11. ± 5.1 | 8.4 ± 1.7 | 1.9 ± 0.3 |

[‡]Data from Epps et al., "A General, Wide-range Spectrofluorometric Method for Measuring the Site-Specific Affinities of Drugs Toward Human Serum Albumin," Analytical Biochemistry, 227:342–50 (1995), which is hereby incorporated by reference in its entirety.

Example 8—Comparison of Intrinsic Fluorescence Measurements to Equilibrium Dialysis Equilibrium dialysis is the usual reference method against which other methods are evaluated (MacKichan, "Influence of Protein Binding and Use of Unbound (Free) Drug Concentrations" in *Applied Pharmacokinetics: Principles of Therapeutic Drug Monitoring*, pp 5.1–5.48, Evans et al. (eds.), Applied Therapeutics, Vancouver, Wash., (1992), which is hereby incorporated by reference in its entirety). In Table 2 below, the dissociation constants obtained using the intrinsic fluorescence method in the preceding Examples were compared to the equilibrium dialysis measurements of the displacement of 5-dimethylaminonapthalene-1-sulfonamide (DNSA) reported by Sudlow et al. (Sudlow et al., "The Characterization of Two Specific Drug Binding Sites on Human Serum Albumin," *Molecular Pharmacology*, 11:824–32 (1975); Sudlow et al., "Further Characterization of Specific Drug Binding Sites on Human Serum Albumin," *Molecular Pharmacology*, 12:1052–61 (1976), which are hereby incorporated by reference in their entirety).

TABLE 2

Comparison of the Equilibrium Dialysis and Intrinsic Fluorescence Methods

| Drug | $K_d$ values ($\mu$M) by Intrinsic Fluorescence | | % DNSA Displacement by Equilibrium Dialysis[†] |
|---|---|---|---|
| | Cuvet | Multiwell | |
| Iophenoxic acid | 0.081 ± 0.012 | Not done | 69.6 |
| Phenylbutazone | 11. ± 5.1 | 8.4 ± 1.7 | 54.6 |
| Sulfinpyrazone | 28. ± 5.6 | 15. ± 3.1 | 29.5 |

[†]Data from Sudlow et al., "The Characterization of Two Specific Drug Binding Sites on Human Serum Albumin," Molecular Pharmacology, 11:824–32 (1975), which is hereby incorporated by reference in its entirety.

The two methods were directly compared using iophenoxic acid, phenylbutazone and sulfinpyrazone binding to HSA in Table 1. The rank order for DNSA displacement was inversely related to the rank order for the dissociation constants, i.e., drugs with lower dissociation constants displace DNSA to a greater extent.

Because a rank order correlation does not always imply a quantitative correlation, the intrinsic fluorescence method was further challenged against the DNSA fluorophore displacement method of equilibrium dialysis using the enantiomers of sodium warfarin. These measurements were carried out in the multiwell format and compared to the results of Sudlow et al (Sudlow ct al., "Further Characterization of Specific Drug Binding Sites on Human Serum Albumin," *Molecular Pharmnacology*, 12:1052–61 (1976) which is hereby incorporated by reference in its entirety). The results, shown below in Table 3, demonstrate that even for compounds that are structurally related, the equilibrium dialysis and intrinsic fluorescence methods correlated well with each other: the enantiomers with higher $K_d$ values caused more DNSA to remain bound.

TABLE 3

Comparison of the Equilibrium Dialysis and Intrinsic Fluorescence Methods for Sodium Warfarin Enantiomers

| Drug | $K_d$ values ($\mu$M) by Intrinsic Fluorescence (Multiwell) | % DNSA bound by Equilibrium Dialysis* |
|---|---|---|
| R(+)-sodium warfarin | 12. ± 2.1 | 68.0 |
| RS-sodium warfarin | 6.8 ± 1.5 | 62.4 |
| S(−)-sodium warfarin | 4.6 ± 0.81 | 60.5 |

*Data from Sudlow et al., "Further Characterization of Specific Drug Binding Sites on Human Serum Albumin," Molecular Pharmacology, 12:1052–61 (1976), which is hereby incorporated by reference in its entirety.

The work of Sudlow and coworkers have also established that the analysis of drugs using fluorophore displacement in equilibrium dialysis method correlates very well with equilibrium dialysis using radio-isotopically labeled drugs. Thus, the findings here suggest that the intrinsic fluorescence method will correlate well with equilibrium dialysis (Sudlow et al., "The Characterization of Two Specific Drug Binding Sites on Human Serum Albumin," *Molecular Pharmacology*, 11:824–32 (1975); Sudlow et al., "Further Characterization of Specific Drug Binding Sites on Human Serum Albumin," *Molecular Pharmacology*, 12:1052–61 (1976), which are hereby incorporated by reference in their entirety).

Example 9—Comparison of Intrinsic Fluorescence Measurements to Drug Binding in Plasma The principal goal of drug binding assays is to determine the fraction of drug bound in plasma at therapeutic concentrations. However, for high throughput screens in discovery, many of the therapeutic parameters are usually unknown and it may be sufficient if a method could simply classify drugs as high, intermediate or poorly bound.

Table 4 compares the dissociation constants for various HSA binding drugs against the percent bound in plasma. The drugs known to be highly bound, warfarin, sulfinpyrazone, phenylbutazone, diazepam and sodium salicylate all had $K_d$ values of less than 100 $\mu$M. The intermediate binding compounds, chloramphenicol and theophylline had $K_d$ values of 150 $\mu$M and 260 $\mu$M, while the poorly bound drugs, acetaminophen, lithium ion, ampicillin either had $K_d$ values greater than 1 mM or did not quench. Thus, the intrinsic fluorescence method is capable of satisfactorily classifying drugs for protein binding characteristics.

TABLE 4

Comparison of Intrinsic Fluorescence $K_d$ Against Percent Bound in Human Plasma

| Drug | Intrinsic Fluorescence, Multiwell $K_d$ ($\mu$M) | % Bound in Plasma[§] |
|---|---|---|
| RS-sodium warfarin | 6.8 ± 1.5 | 99 ± 1 |
| Phenylbutazone | 8.4 ± 1.7 | 96 ± 1 |
| Sulfinpyrazone | 15. ± 3.2 | 98 ± 0.3 |
| Diazepam | 28 ± 4 | 98.7 ± 0.2 |
| Sodium salicylate | 71 ± 12 | 80 to 95 |
| Theophylline | 260 ± 92 | 56 ± 4 |
| Chloramphenicol | 150 ± 48 | 53 ± 5 |
| Acetaminophen | 1279 ± 690 | 0 |
| Lithium chloride | No quenching | 0 |
| Ampicillin | No quenching | 18 |

[§]Data from Goodman and Gilman's The Pharmacological Basis of Therapeutics, Hardman et al (eds.), McGraw-Hill, Health Professions, New York (1996), which is hereby incorporated by reference in its entirety.

Example 10—Correction of the Inner Filter Effect

In fluorescence measurements, the inner filter effect (caused by the absorbance contributions of protein and drug) can be a potentially serious confounding factor and is usually compensated for by making concurrent absorbance measurements (Lakowicz, *Principles of Fluorescence Spectroscopy*, Plenum Press, New York, N.Y. (1983), which is hereby incorporated by reference in its entirety). Because additional absorbance measurements would add another step to the screen and potentially reduce its throughput, other approaches were used to reduce the impact of the inner filter effect. First, the albumin fluorescence was examined as a function of concentration over the range of 0–100 $\mu$M in the absence of drug. Because of the inner filter effect, the albumin intrinsic fluorescence showed apparent saturation and, functionally, these observations could be modeled using a simple $E_{max}$ or Michaelis-Menten equation ($r^2 > 0.99$). The range of $EC_{50}$ values from the fitting was 27 $\mu$M to 36 $\mu$M and based on these values, the 2 $\mu$M HSA concentration used in the experiments was 6–7% of $EC_{50}$- within the linear range. Secondly, to ensure uniform illumination, a 2 mm path length cuvet was used. These decisions were supported post facto by the excellent correspondence between the fluorescence method and the other approaches.

Ultimately, the inner filter effect can be rigorously corrected by serially processing samples through a multiwell fluorimeter and a multiwell absorbance spectrophotometer. However, two-site and multi-site models for fitting were not used in the analysis of the present results, because the regression coefficients were usually greater than 95% and the addition of parameters frequently caused some parameters to lose statistical significance.

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. A method of screening for drug binding to serum proteins, said method comprising:
    preparing at least two solutions, each of said at least two solutions comprising a concentration of a gerum protein characterized by broad specificity in binding to xenobiotics and a concentration of a candidate drug, wherein the concentration of the candidate drug is different for each of the at least two solutions and, optionally, one of the at least two solutions is a control solution characterized by a candidate drug concentration of zero;
    exposing each of the at least two solutions to a light source;
    measuring fluorescent emission by the serum protein or a serum protein-candidate drug complex for each of the at least two solutions upon said exposing; and
    determining whether a change in fluorescence emission is measured for an increased concentration of the candidate drug, wherein the change in fluorescence emission indicates binding of the candidate drug to the serum protein.

2. The method according to claim 1, wherein said determining further comprises:
    determining a minimal concentration of the candidate drug to produce a maximal change in fluorescence.

3. The method according to claim 1, wherein the serum protein comprises one or more tryptophan or tyrosine residues.

4. The method according to claim 3, wherein the serum protein is an albumin, a glycoprotein, a lipoprotein, or a combination thereof.

5. The method according to claim 3, wherein the serum protein is human serum albumin or human $\alpha_1$-acid glycoprotein.

6. The method according to claim 1, wherein the light source emits light at a wavelength of about 280 nm.

7. The method according to claim 1, wherein said measuring fluorescent emission comprises measuring emission maxima in the range of about 300 nm to about 400 nm.

8. The method according to claim 7, wherein the emission maxima are at a wavelength of about 340 nm.

9. The method according to claim 1, wherein each of the at least two solutions is an aqueous solution.

10. The method according to claim 1, wherein each of the at least two solutions comprises dimethyl sulfoxide (DMSO) as a solvent.

11. The method according to claim 1, further comprising:
calculating a dissociation constant ($K_d$) for the candidate drug and the serum protein.

12. The method according to claim 1, wherein the concentration of the serum protein in each of the at least two solutions is substantially the same.

13. The method according to claim 1, wherein the candidate drug is one of a plurality of candidate drugs, said preparing comprises preparing a series of the at least two solutions for each of the plurality of candidate drugs, said exposing and measuring are carried out in a multiwell format, and said determining is carried out for each of the plurality of candidate drugs.

14. The method according to claim 1, wherein said measuring is specific for a fluorescent emission maxima of unbound serum protein and wherein the change in fluorescent emission by unbound serum protein is a reduction of the fluorescent emission for an increase in candidate drug concentration.

15. The method according to claim 1, wherein said measuring is specific for a fluorescent emission maxima of serum protein bound to the candidate drug and wherein the change in fluorescent emission by the serum protein bound to the candidate drug is an increase of the fluorescent emission for an increase in the candidate drug concentration.

16. A method of screening for drug binding to serum proteins, said method comprising:
preparing at least two solutions, each of said at least two solutions comprising a concentration of a serum protein characterized by broad specificity in binding to xenobiotics and a concentration of a candidate drug, wherein the concentration of the candidate drug is different for each of the at least two solutions and, optionally, one of the at least two solutions is a control solution characterized by a candidate drug concentration of zero;
exposing each of the at least two solutions to a light source;
measuring fluorescent emission by the serum protein or a serum protein-candidate drug complex for each of the at least two solutions upon said exposing; and
calculating a dissociation constant ($K_d$) for the candidate drug and the serum protein based on the measured fluorescence emissions.

17. The method according to claim 16, wherein the serum protein comprises one or more tryptophan or tyrosine residues.

18. The method according to claim 17, wherein the serum protein is an albumin, a glycoprotein, a lipoprotein, or a combination thereof.

19. The method according to claim 17, wherein the serum protein human serum albumin or human $\alpha_1$-acid glycoprotein.

20. The method according to claim 16, wherein the light source its light at a wavelength of about 280 nm.

21. The method according to claim 16, wherein said measuring fluorescent emission comprises measuring emissions in the range of about 300 nm to about 400 nm.

22. The method according to claim 21, wherein the emissions are at a wavelength of about 340 nm.

23. The method according to claim 16, wherein each of the at least two solutions is an aqueous solution.

24. The method according to claim 16, wherein each of the at least two solutions comprises dimethyl sulfoxide (DMSO) as a solvent.

25. The method according to claim 16, wherein the concentration of the serum protein in each of the at least two solutions is substantially the same.

26. The method according to claim 16, wherein the candidate drug is one of a plurality of candidate drugs, said preparing comprises preparing a series of the at least two solutions for each of the plurality of candidate drugs, said exposing and measuring are carried out in a multiwell format, and said determining is carried out for each of the plurality of candidate drugs.

27. A kit useful for performing a fluorimetric screening of drug binding to serum proteins, the kit comprising:
a plurality of detection cells compatible for use with a fluorimetric device;
one or more solutions each comprising a predetermined concentration of a serum protein characterized by broad specificity in binding to xenobiotics; and
instructions for combining a volume of the one or more solutions with a quantity of a drug in the detection cells, exposing the detection cells to the fluorimetric device, and analyzing fluorimetric emission data.

28. The kit according to claim 27, wherein the detection cells are cuvettes.

29. The kit according to claim 27, wherein the detection cells are multiwell plates.

30. The kit according to claim 27, wherein the serum protein comprises one or more tryptophan or tyrosine residues.

31. The kit according to claim 30, wherein the serum protein is an albumin, a glycoprotein, a lipoprotein, or a combination thereof.

32. The kit according to claim 30, wherein the serum protein is human serum albumin or human $\alpha_1$-acid glycoprotein.

* * * * *

UNITED STATES PATENT AND TRADEMARK OFFICE
CERTIFICATE OF CORRECTION

PATENT NO.    : 6,468,757 B2
DATED         : October 22, 2002
INVENTOR(S)   : Murali Ramanathan and Marilyn E. Morris It is certified that error appears in the above-identified patent and that said Letters Patent is hereby corrected as shown below:

Column 14,
Line 30, "gerum" should be -- serum --.

Column 16,
Line 8, "its" should be -- emits --.

Signed and Sealed this

Eighteenth Day of March, 2003

JAMES E. ROGAN
*Director of the United States Patent and Trademark Office*